United States Patent
Olson et al.

(10) Patent No.: US 11,039,963 B2
(45) Date of Patent: Jun. 22, 2021

(54) ABSORBENT ARTICLE WITH MECHANICAL GARMENT ATTACHMENT

(71) Applicant: Kimberly-Clark Worldwide, Inc., Neenah, WI (US)

(72) Inventors: Christopher Peter Olson, Neenah, WI (US); Suzanne Marie Schmoker, Neenah, WI (US); Cynthia H. Hendren, Neenah, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 848 days.

(21) Appl. No.: 15/580,917

(22) PCT Filed: Jun. 22, 2016

(86) PCT No.: PCT/US2016/038692
§ 371 (c)(1),
(2) Date: Dec. 8, 2017

(87) PCT Pub. No.: WO2016/209914
PCT Pub. Date: Dec. 29, 2016

(65) Prior Publication Data
US 2020/0038265 A1 Feb. 6, 2020

Related U.S. Application Data

(60) Provisional application No. 62/184,092, filed on Jun. 24, 2015.

(51) Int. Cl.
A61F 13/476 (2006.01)
A61F 13/56 (2006.01)

(52) U.S. Cl.
CPC ........ *A61F 13/5616* (2013.01); *A61F 13/476* (2013.01)

(58) Field of Classification Search
CPC .... A61F 13/47; A61F 13/476; A61F 13/5605; A61F 13/5611; A61F 13/5616
See application file for complete search history.

(56) References Cited

U.S. PATENT DOCUMENTS 3,397,697 A 8/1968 Rickard
5,201,727 A * 4/1993 Nakanishi ............. A61F 13/476
604/358

(Continued)

FOREIGN PATENT DOCUMENTS

CN 1131386 A 9/1996
CN 203915242 U 11/2014

(Continued)

*Primary Examiner* — Catharine L Anderson
*Assistant Examiner* — Lynne Anderson
(74) *Attorney, Agent, or Firm* — Kimberly-Clark Worldwide, Inc.

(57) ABSTRACT

An absorbent article can have an improved attachment to a wearer's undergarment and can maintain proper placement in the undergarment of the wearer. The absorbent article can produce less waste for the wearer of the absorbent article. The absorbent article can have a topsheet layer, a backsheet layer, an absorbent core positioned between the topsheet layer and the backsheet layer, and a pair of opposing wings. The absorbent article can have a mechanical garment attachment which can maintain the placement of the absorbent article within the wearer's undergarment.

14 Claims, 7 Drawing Sheets

(56) References Cited

U.S. PATENT DOCUMENTS

| | | |
|---|---|---|
| 5,300,058 A | 4/1994 | Goulait et al. |
| 5,346,486 A | 9/1994 | Osborn, III et al. |
| 5,401,268 A | 3/1995 | Rodier |
| 5,584,829 A | 12/1996 | Lavash et al. |
| 5,611,790 A | 3/1997 | Hines et al. |
| 5,676,652 A | 10/1997 | Hunter et al. |
| 5,681,304 A | 10/1997 | Van Iten |
| 5,713,886 A | 2/1998 | Sturino |
| 5,972,806 A | 10/1999 | Weinberger et al. |
| 6,077,255 A | 6/2000 | Hunter et al. |
| 6,287,288 B1 | 9/2001 | Osborn, III et al. |
| 6,416,502 B1 | 7/2002 | Connelly et al. |
| 6,524,422 B2 | 2/2003 | Helmfridsson et al. |
| 6,554,812 B2 | 4/2003 | Drevik |
| 6,569,138 B2 | 5/2003 | Helmfridsson et al. |
| 6,586,654 B2 | 7/2003 | Drevik |
| 6,602,237 B2 | 8/2003 | Helmfridsson et al. |
| 6,843,785 B2 | 1/2005 | Hammonds et al. |
| 8,486,037 B2 * | 7/2013 | Konawa ............ A61F 13/47245 604/385.05 |
| D692,557 S | 10/2013 | Niemeyer et al. |
| 2003/0040731 A1 | 2/2003 | Nozaki et al. |
| 2004/0236298 A1 | 11/2004 | Coates |
| 2005/0020994 A1 | 1/2005 | Ng et al. |
| 2005/0080392 A1 | 4/2005 | Ng et al. |
| 2005/0131372 A1 | 6/2005 | Wheeler et al. |
| 2005/0283131 A1 | 12/2005 | Zander et al. |
| 2006/0052762 A1 | 3/2006 | Ng et al. |
| 2008/0249496 A1 | 10/2008 | Petersen et al. |
| 2013/0304013 A1 | 11/2013 | Goerg-Wood et al. |
| 2014/0213996 A1 | 7/2014 | Petersen et al. |
| 2014/0343525 A1 | 11/2014 | Roh et al. |

FOREIGN PATENT DOCUMENTS

| | | | |
|---|---|---|---|
| EP | 0607986 A1 | 7/1994 | |
| EP | 0511905 B1 | 8/1995 | |
| EP | 0840586 B1 | 12/2001 | |
| EP | 1181917 A2 | 2/2002 | |
| JP | 2004290602 A * | 10/2004 | ......... A61F 13/5616 |
| WO | WO 2010/110270 A1 | 9/2010 | |

* cited by examiner

ABSORBENT ARTICLE WITH MECHANICAL GARMENT ATTACHMENT

RELATED APPLICATIONS

The present application claims priority to U.S. Provisional Application No. 62/184,092, filed on Jun. 25, 2015, the contents of which are hereby incorporated by reference in a manner consistent with the present application.

BACKGROUND

Products such as absorbent articles are often used to collect and retain human body exudates containing, for example, urine, menses and/or blood. Comfort, absorbency, and discretion are three main product attributes and areas of concern for the wearer of the product. In particular, a wearer is often interested in knowing that such products will absorb significant volumes of body exudates with minimal leakage in order to protect their undergarments, outer garments, or bedsheets from staining, and that such products will help them avoid the subsequent embarrassment brought on by such staining.

Currently, a wide variety of products for absorption of body exudates are available in the form of feminine pads, sanitary napkins, panty shields, pantiliners, and incontinence devices. These products generally have an absorbent core positioned between a body-facing liquid permeable topsheet layer and a garment-facing liquid impermeable backsheet layer. The edges of the topsheet and the backsheet layers are often bonded together at their periphery to form a seal to contain the absorbent core and body exudates received into the product through the topsheet layer. In use, such products are typically positioned in the crotch portion of an undergarment for absorption of the body exudates and a garment attachment adhesive on the backsheet layer can be used to attach the product to the inner crotch portion of the undergarment. Some of these products can also include wings for wrapping about the wearer's undergarment to further secure the product to the undergarment and to protect the undergarment from staining. Such wings are frequently made from lateral extensions of the topsheet and/or backsheet layers.

Drawbacks exist, however, with utilizing a garment attachment adhesive to maintain the placement of such products within the wearer's undergarment. Utilizing a garment attachment adhesive further requires the utilization of protective release sheets which overlay the garment attachment adhesive and will maintain the garment attachment adhesive in a clean configuration prior to usage of the product. In order for the wearer to use the product, however, the wearer must remove the protective release sheets to expose the garment attachment adhesive and then discard the protective release sheets as waste. Once the protective release sheets have been removed and the garment attachment adhesive has been exposed, any distortion/twisting/bunching of the product which can occur prior to the placement of the product into the wearer's undergarment can result in sections of the garment attachment adhesive becoming stuck together which can render the product non-useable. Even in situations where the wearer may be able to peel the stuck together sections of the product apart, the product may have residual distortions/twisting/bunching which can diminish the capability of the product to perform as expected. An additional drawback is the garment attachment adhesive can stick to the skin and/or body hair of the wearer causing irritations to the wearer. A further drawback is the potential for the garment attachment adhesive to have diminished adhesive properties should the garment attachment adhesive come into contact with perspiration or other fluids. Such diminished adhesive properties can result in the product becoming detached from the wearer's undergarment which can also diminish the capability of the product to perform as expected.

A need exists for an absorbent article which can have an improved attachment to a wearer's undergarment. A need exists for an absorbent article which can produce less waste for the wearer of the absorbent article. A need exists for an absorbent article which can maintain proper placement in the undergarment of the wearer.

SUMMARY

In various embodiments, an absorbent article can have a longitudinal axis and a transverse axis; an anterior portion, a posterior portion, and a central portion extending between the anterior portion and the posterior portion; a topsheet layer, a backsheet layer, and an absorbent core positioned between the topsheet layer and the backsheet layer; a first wing extending in a first transverse direction and a second wing extending in a second transverse direction which is opposite the first transverse direction; a pair of opposing primary garment attachment regions, each of the primary garment attachment regions having a first segment positioned in a chassis area of the absorbent article, a second segment positioned in a wing folding area of the absorbent article, and a third segment positioned in a wing area of the absorbent article; and a mechanical garment attachment positioned within each of the primary garment attachment regions. In various embodiments, each primary garment attachment region has a primary garment attachment region angle relative to the longitudinal axis from about 15 degrees to about 70 degrees. In various embodiments, each primary garment attachment region has a width from about 2 mm to about 15 mm. In various embodiments, each primary garment attachment region has a length from about 20 mm to about 90 mm. In various embodiments, the absorbent article can further have a second pair of opposing primary garment attachment regions.

In various embodiments, the absorbent article can further have a pair of opposing secondary garment attachment regions. In various embodiments, the pair of opposing secondary garment attachment regions are positioned in the anterior portion of the absorbent article. In various embodiments, the pair of opposing secondary garment attachment regions are positioned in the posterior portion of the absorbent article. In various embodiments, each of the secondary garment attachment regions has a secondary garment attachment region angle relative to the longitudinal axis from about 15 degrees to about 70 degrees. In various embodiments, each of the secondary garment attachment regions has a width from about 2 mm to about 15 mm. In various embodiments, each of the secondary garment attachment regions has a length from about 15 mm to about 50 mm.

In various embodiments, the second segment of each of the primary garment attachment regions comprises a plurality of mechanical garment attachments positioned therein wherein the mechanical garment attachments are positioned in a plurality of rows of the mechanical garment attachments and a first row of plurality of rows of the mechanical garment attachments is in a spaced apart configuration from a second row of the plurality of rows of the mechanical garment attachments.

In various embodiments, the mechanical garment attachment is bonded directly to a base substrate wherein the base substrate is bonded directly to the backsheet layer of the absorbent article. In various embodiments, a score line is incorporated into the base substrate.

DETAILED DESCRIPTION

Figure 1:
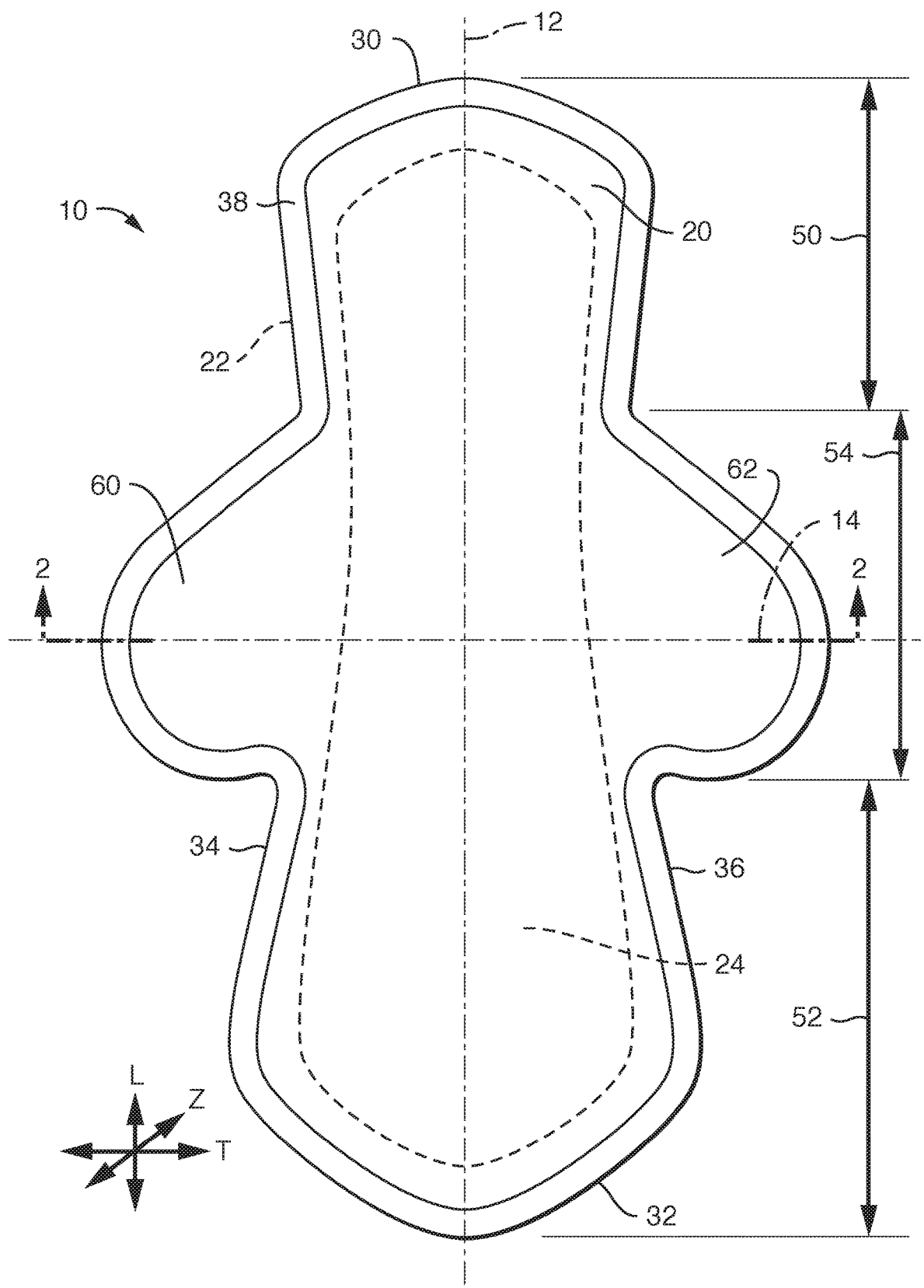
FIG. 1 is a top view of an embodiment of an absorbent article.

The present disclosure is generally directed towards an absorbent article which can have an improved attachment to the wearer's undergarment and which can maintain proper placement in the undergarment of the wearer. The absorbent article described herein can produce less waste for the wearer of the absorbent article. The absorbent article described herein can have a topsheet layer, a backsheet layer, an absorbent core positioned between the topsheet layer and the backsheet layer, and a pair of opposing wings. The absorbent article can have a mechanical garment attachment which can maintain the placement of the absorbent article within the wearer's undergarment.

Definitions:

As used herein, the term "absorbent article" refers herein to a garment or other end-use personal care absorbent article, including, but not limited to, catamenial products, such as sanitary napkins, feminine pads, pantiliners, and panty shields, incontinence devices, and the like.

As used herein, the term "airlaid" refers herein to a web manufactured by an airlaying process. In the airlaying process, bundles of small fibers having typical lengths ranging from about 3 to about 52 mm are separated and entrained in an air supply and then deposited onto a forming screen, usually with the assistance of a vacuum supply. The randomly deposited fibers are then bonded to one another using, for example, hot air to activate a binder component or a latex adhesive. Airlaying is taught in, for example, U.S. Pat. No. 4,640,810 to Laursen, et al., which is incorporated herein in its entirety by reference thereto for all purposes.

As used herein, the term "bonded" refers herein to the joining, adhering, connecting, attaching, or the like, of two elements. Two elements will be considered bonded together when they are joined, adhered, connected, attached, or the like, directly to one another or indirectly to one another, such as when bonded to an intermediate element. The bonding can occur via, for example, adhesive, pressure bonding, thermal bonding, ultrasonic bonding, stitching, suturing, and/or welding.

As used herein, the term "bonded carded web" refers herein to webs that are made from staple fibers which are sent through a combing or carding unit which separates or breaks apart and aligns the staple fibers in the machine direction to form a generally machine direction oriented fibrous nonwoven web. This material may be bonded together by methods that can include point bonding, through air bonding, ultrasonic bonding, adhesive bonding, etc.

As used herein, the term "coform" refers herein to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff, and also superabsorbent particles, inorganic and/or organic absorbent materials, treated polymeric staple fibers and so forth. Some examples of such coform materials are disclosed in U.S. Pat. No. 4,100,324 to Anderson, et al., U.S. Pat. No. 4,818,464 to Lau, U.S. Pat. No. 5,284,703 to Everhart, et al., and U.S. Pat. No. 5,350,624 to Georger, et al., each of which are incorporated herein in their entirety by reference thereto for all purposes.

As used herein, the term "conjugate fibers" refers herein to fibers which have been formed from at least two polymer sources extruded from separate extruders and spun together to form one fiber. Conjugate fibers are also sometimes referred to as bicomponent fibers or multicomponent fibers. The polymers are arranged in substantially constantly positioned distinct zones across the cross-sections of the conjugate fibers and extend continuously along the length of the conjugate fibers. The configuration of such a conjugate fiber may be, for example, a sheath/core arrangement where one polymer is surrounded by another, or may be a side-by-side arrangement, a pie arrangement, or an "islands-in-the-sea" arrangement. Conjugate fibers are taught by U.S. Pat. No. 5,108,820 to Kaneko, et al., U.S. Pat. No. 4,795,668 to Krueger, et al., U.S. Pat. No. 5,540,992 to Marcher, et al., U.S. Pat. No. 5,336,552 to Strack, et al., U.S. Pat. No. 5,425,987 to Shawver, and U.S. Pat. No. 5,382,400 to Pike, et al. each being incorporated herein in their entirety by reference thereto for all purposes. For two component fibers, the polymers may be present in ratios of 75/25, 50/50, 25/75 or any other desired ratio. Additionally, polymer additives such as processing aids may be included in each zone.

As used herein, the term "machine direction" (MD) refers to the length of a fabric in the direction in which it is produced, as opposed to a "cross-machine direction" (CD) which refers to the width of a fabric in a direction generally perpendicular to the machine direction.

As used herein, the term "meltblown web" refers herein to a nonwoven web that is formed by a process in which a molten thermoplastic material is extruded through a plurality of fine, usually circular, die capillaries as molten fibers into converging high velocity gas (e.g., air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin, et al., which is incorporated herein in its entirety by reference thereto for all purposes. Generally speaking, meltblown fibers may be microfibers that are substantially continuous or discontinuous, generally smaller than 10 microns in diameter, and generally tacky when deposited onto a collecting surface.

As used herein, the term "nonwoven fabric" or "nonwoven web" refers herein to a web having a structure of individual fibers or threads which are interlaid, but not in an identifiable manner as in a knitted fabric. Nonwoven fabrics or webs have been formed from many processes such as, for example, meltblowing processes, spunbonding processes, through-air bonded carded web (also known as BCW and TABCW) processes, etc. The basis weight of nonwoven webs may generally vary, such as, from about 5, 10 or 20 gsm to about 120, 125 or 150 gsm.

As used herein, the term "spunbond web" refers herein to a web containing small diameter substantially continuous fibers. The fibers are formed by extruding a molten thermoplastic material from a plurality of fine, usually circular, capillaries of a spinneret with the diameter of the extruded fibers then being rapidly reduced as by, for example, eductive drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are each incorporated herein in their entirety by reference thereto for all purposes. Spunbond fibers are generally not tacky when they are deposited onto a collecting surface. Spunbond fibers may sometimes have diameters less than about 40 microns, and often between about 5 to about 20 microns.

As used herein, the terms "superabsorbent polymer," "superabsorbent" or "SAP" shall be used interchangeably and shall refer to polymers that can absorb and retain extremely large amounts of a liquid relative to their own mass. Water absorbing polymers, which are classified as hydrogels, which can be cross-linked, absorb aqueous solutions through hydrogen bonding and other polar forces with water molecules. A SAP's ability to absorb water is based in part on ionicity (a factor of the ionic concentration of the aqueous solution), and the SAP functional polar groups that have an affinity for water. SAP are typically made from the polymerization of acrylic acid blended with sodium hydroxide in the presence of an initiator to form a poly-acrylic acid sodium salt (sometimes referred to as sodium polyacrylate). Other materials are also used to make a superabsorbent polymer, such as polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile. SAP may be present in absorbent articles in particle or fibrous form or as a coating on another material or fiber.

Absorbent Article:

The present disclosure is generally directed towards an absorbent article which can have an improved attachment to the wearer's undergarment and which can maintain proper placement in the undergarment of the wearer. The absorbent article described herein can produce less waste for the wearer of the absorbent article. The absorbent article described herein can have a topsheet layer, a backsheet layer, an absorbent core positioned between the topsheet layer and the backsheet layer, and a pair of opposing wings. The absorbent article can have a mechanical garment attachment which can maintain the placement of the absorbent article within the wearer's undergarment.

Figure 2:
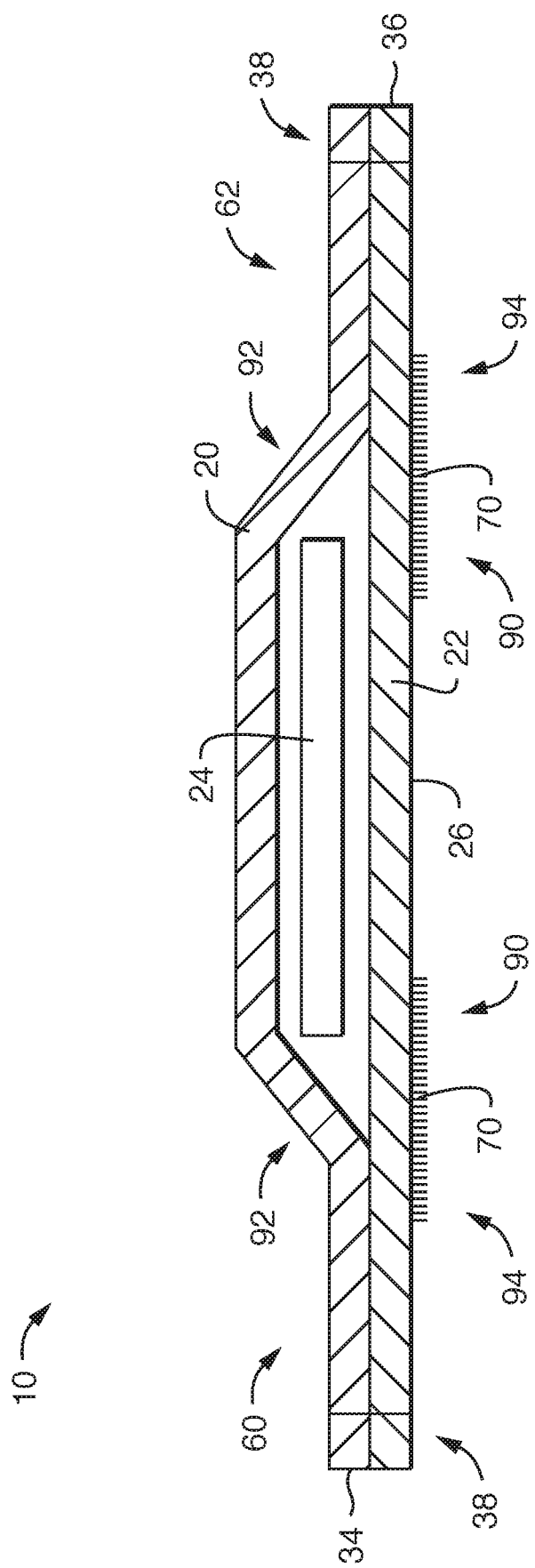
FIG. 2 is a cross-sectional view of the absorbent article of FIG. 1 taken along line 2-2.
Figure 3:
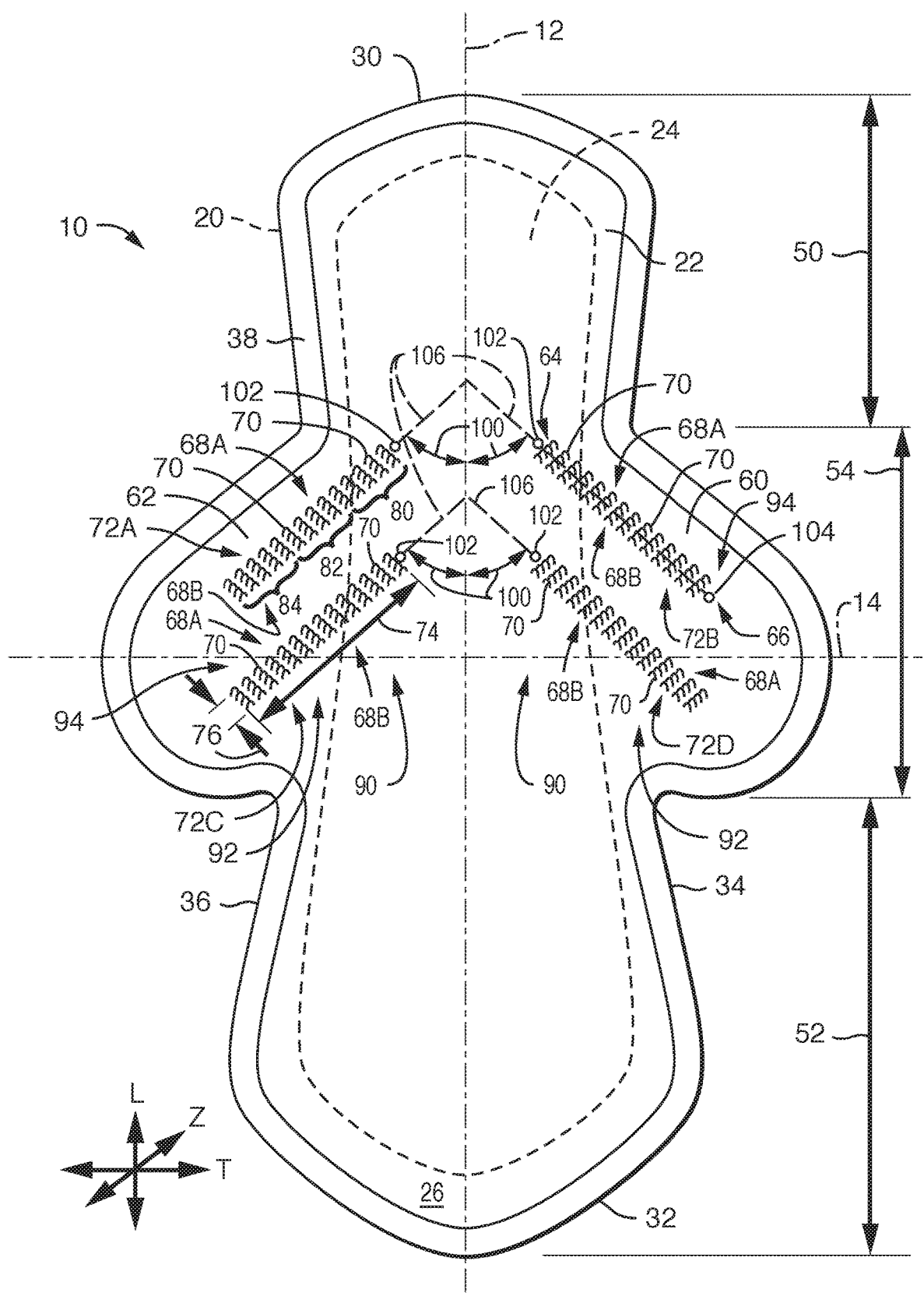
FIG. 3 is a bottom view of an embodiment of the absorbent article of FIG. 1 in a first configuration, such as an unfolded and laid-flat configuration.
Figure 4:
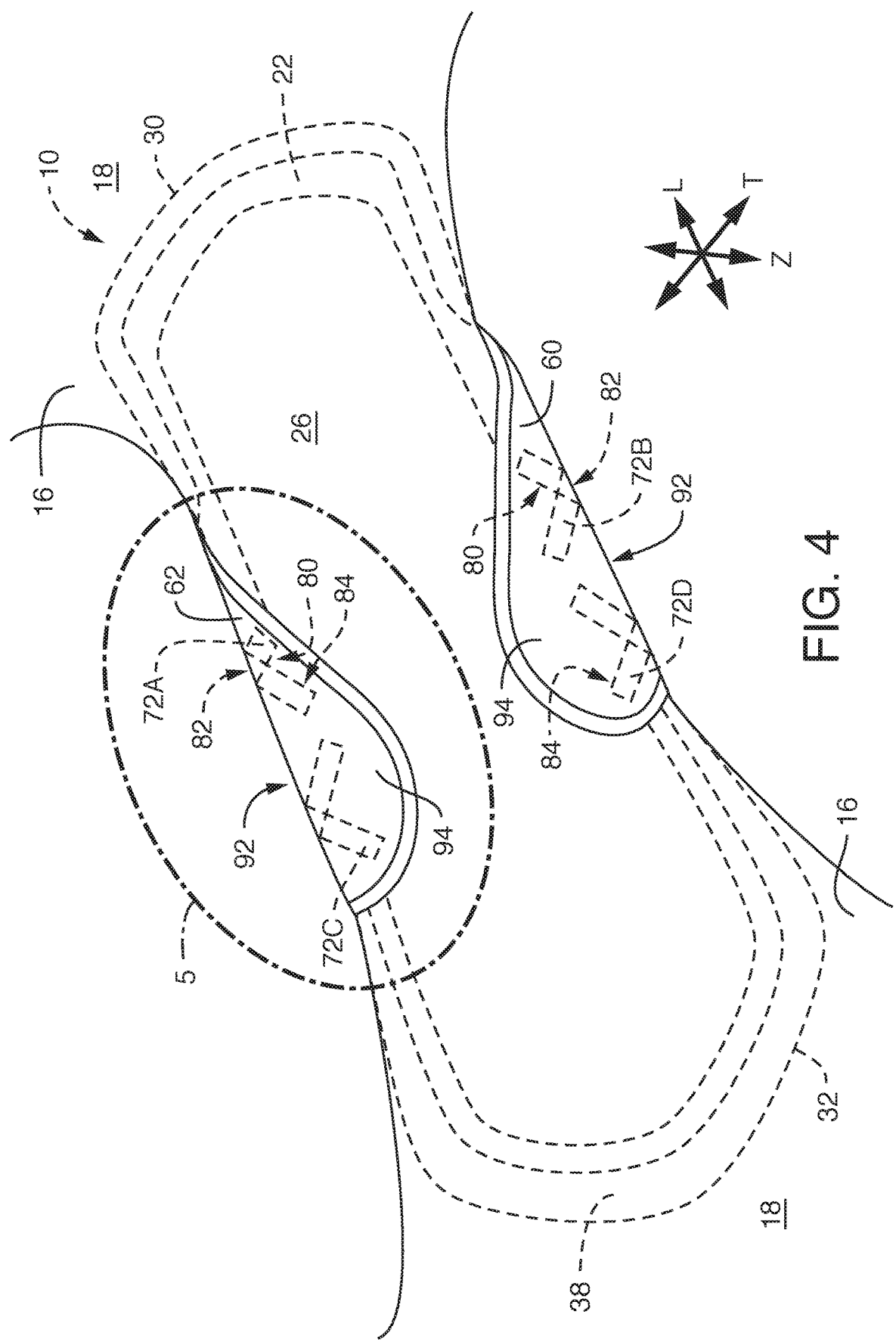
FIG. 4 is a perspective bottom view of the absorbent article of FIG. 1 in a second configuration, such as an in-use configuration in which the wings are folded over and onto the garment facing surface of a wearer's undergarment.

Referring to FIGS. 1-4, FIG. 1 provides an illustration of a top view of an exemplary embodiment of an absorbent article 10, FIG. 2 provides an illustration of a cross-sectional view of the absorbent article 10 of FIG. 1 taken along line 2-2, FIG. 3 provides an illustration of a bottom view of an embodiment of the absorbent article 10 of FIG. 1 in a first configuration, such as an unfolded and laid-flat configuration, and FIG. 4 provides a perspective bottom view of the absorbent article 10 of FIG. 1 in a second configuration such as an in-use configuration in which the absorbent article 10 is fitted into a wearer's undergarment 16 with the wings folded over and onto the garment facing surface 18 of the wearer's undergarment 16.

The absorbent article 10 can have a longitudinal direction (L), a transverse direction (T), and a depth direction (Z). The absorbent article 10 can have a longitudinal axis 12 and a transverse axis 14. The absorbent article 10 can have a wearer facing, liquid permeable topsheet layer 20 and a garment facing, liquid impermeable backsheet layer 22. An absorbent core 24 can be positioned between the topsheet layer 20 and the backsheet layer 22. The absorbent article 10 can have a first transverse direction end edge 30, a second transverse direction end edge 32 opposite the first transverse direction end edge 30, and a pair of opposing longitudinal direction side edges, 34 and 36. In various embodiments, the absorbent article 10 can take on various geometries but will generally have a pair of opposing transverse direction end edges, 30 and 32, and a pair of opposing longitudinal direction side edges, 34 and 36.

The topsheet layer 20 and the backsheet layer 22 can both extend beyond the outermost peripheral edges of the absorbent core 24 and can be peripherally bonded together, either entirely or partially, using known bonding techniques to form a sealed peripheral region 38. For example, the topsheet layer 20 and the backsheet layer 22 can be bonded together by adhesive bonding, ultrasonic bonding, or any other suitable bonding method known in the art.

The absorbent article 10 can have an anterior portion 50, a posterior portion 52, and a central portion 54 extending between the anterior portion 50 and the posterior portion 52. In general, the anterior portion 50 of the absorbent article 10 is adapted to be worn towards the front of the wearer, the central portion 54 is adapted to be worn proximate the wearer's crotch, and the posterior portion 52 is adapted to be worn towards the rear of the wearer. In various embodiments, the absorbent article 10 can have a length as measured in the longitudinal direction (L) between the transverse direction end edges, 30 and 32, and the anterior portion 50 can be defined as the front third of the absorbent article length, the central portion 54 can be defined as the center third of the absorbent article length, and the posterior portion 52 can be defined as the rear third of the absorbent article length. It is to be understood that the lengths of each of the anterior portion 50, the central portion 54 and the posterior portion 52 can vary as deemed suitable for usage of the absorbent article 10.

In various embodiments, the absorbent article 10 can have a pair of wings, 60 and 62, extending outwardly, in the transverse direction (T), from the absorbent article 10. The wings, 60 and 62, can be folded downwardly in wing folding areas 92 and can drape over the edges of the wearer's undergarment so that the wings, 60 and 62, are disposed between the edges of the wearer's undergarment and her thighs. The wings, 60 and 62, can prevent soiling of the wearer's undergarment by forming a barrier along the edges of the undergarment. In various embodiments, the wings, 60 and 62, can be an extension of materials forming the topsheet layer 20 and/or the backsheet layer 22, such that the wings, 60 and 62, can be of a unitary construction with the absorbent article 10. In various embodiments, the wings, 60 and 62, can be constructed of materials similar to the topsheet layer 20, the backsheet layer 22 or combinations of these materials. In various embodiments, the wings, 60 and 62, can be separate elements bonded to the main body of the absorbent article 10.

The absorbent article 10 can be provided with a primary mechanical garment attachment 70 such as, for example, a hook, to keep the absorbent article 10 securely and properly positioned in the wearer's undergarment. The primary mechanical garment attachment 70 can be positioned in a primary garment attachment region 72 and can be located on a garment facing surface 26 of the absorbent article 10. In various embodiments, the absorbent article 10 can have at least one pair of opposing primary garment attachment regions, 72A and 72B. In various embodiments, such as, for example, illustrated in FIGS. 3 and 4, the absorbent article 10 can have at least two pairs of opposing primary garment attachment regions, first pair 72A and 72B and second pair 72C and 72D. Each primary garment attachment region 72 can have a leading portion 64, defined by the primary mechanical garment attachment 70 closest to the longitudinal axis 12, and a trailing portion 66, defined by the primary mechanical garment attachment 70 furthest from the longitudinal axis 12. Each primary garment attachment region 72 can have a length 74 which can be measured as the distance from the leading portion 64 to the training portion 66. Each primary garment attachment region 72 can also have a pair of opposing side portions, 68A and 68B, which extend between and connect the leading portion 64 to the trailing portion 66 of the primary garment attachment region 72. Each primary garment attachment region 72 can have a width 76 which can be measured as the distance between the opposing side portions, 68A and 68B. The length 74 and width 76 of each primary garment attachment region 72 can provide an area for each primary attachment region 72 which can contain the primary mechanical garment attachment 70.

The length 74 of each of the primary garment attachment regions 72 can be divided into three segments: a first segment 80, a second segment 82 and a third segment 84. In various embodiments, each of the three segments, 80, 82 and 84, can be equal in length. In various embodiments, two of the three segments, 80, 82 or 84, can be equal in length and one of the three segments, 80, 82 or 84, can have a length different from the other two segments. In various embodiments, each of the three segments, 80, 82 and 84, can have a length different from each of the other segments, 80, 82 and 84. The first segment 80 of the primary garment attachment region 72 can be the portion of the primary garment attachment region 72 positioned in a chassis area 90 of the absorbent article 10 and which underlays the absorbent core 24 when viewing the absorbent article 10 in a top down configuration. The primary mechanical garment attachment 70 positioned in the first segment 80 of the primary garment attachment region 72 can maintain contact between the absorbent article 10 and the wearer facing surface of the wearer's undergarment 16 when the absorbent article 10 is in a second configuration such as a usage configuration. The second segment 82 of the primary garment attachment region 72 can be the portion of the primary garment attachment region 72 positioned in the wing folding area 92. The primary mechanical garment attachment 70 positioned in the second segment 82 of the primary garment attachment region 72 can maintain contact between the absorbent article 10 and each of the surfaces of the seams of the wearer's undergarment 16—the wearer facing surface of the seam, the thigh facing surface of the seam and the garment facing surface of the seam when the absorbent article 10 is in a second configuration such as a usage configuration. The third segment 84 of the primary garment attachment region 72 can be the portion of the primary garment attachment region 72 positioned in a wing area 94. The primary mechanical garment attachment 70 positioned in the third segment 84 of the primary garment attachment region 72 can maintain contact between the absorbent article 10 and the garment facing surface 18 of the wearer's undergarment 16 when the absorbent article 10 is in a second configuration such as a usage configuration.

Each of the primary garment attachment regions 72 can be configured to provide the absorbent article 10, in a first configuration such as an unfolded and flat configuration, with a primary garment attachment region angle 100. The primary garment attachment region angle 100 is the angle between the longitudinal axis 12 and a line 106 that connects the middle-width 104 at the trailing portion 66 of the primary garment attachment region 72 with the middle-width 102 at the leading portion 64 of the primary garment attachment region 72 and then extends to the longitudinal axis 12. The primary garment attachment region angle 100, relative to the longitudinal axis 12 of the absorbent article 10, can be from about 15 degrees to about 70 degrees. To convert the absorbent article 10 from the first configuration to the second configuration, each wing, 60 and 62, can be folded downwardly in the wing folding areas 92 and fold under the crotch region of the wearer's undergarment and the primary mechanical garment attachment 70 can form a secure attachment to the surface of the wearer's undergarment 16 via each of the three segments, 80, 82 and 84, of the primary garment attachment region 72.

Each of these components of the absorbent article 10, as well as additional components, will be described in more detail herein.

Topsheet Layer:

The topsheet layer 20 defines a wearer facing surface of the absorbent article 10 that may directly contact the body of the wearer and is liquid permeable to receive body exudates. The topsheet layer 20 is desirably provided for comfort and conformability and functions to direct body exudates away from the body of the wearer, through its own structure, and towards the absorbent core 24. The topsheet layer 20 desirably retains little to no liquid in its structure, so that it provides a relatively comfortable and non-irritating surface next to the skin of the wearer of the absorbent article 10.

The topsheet layer 20 can be a single layer of material, or alternatively, can be multiple layers that have been laminated together. The topsheet layer 20 can be constructed of any material such as one or more woven sheets, one or more fibrous nonwoven sheets, one or more film sheets, such as blown or extruded films, which may themselves be of single or multiple layers, one or more foam sheets, such as reticulated, open cell or closed cell foams, a coated nonwoven sheet, or a combination of any of these materials. Such combination can be adhesively, thermally, or ultrasonically laminated into a unified planar sheet structure to form a topsheet layer 20.

In various embodiments, the topsheet layer 20 can be constructed from various nonwoven webs such as meltblown webs, spunbond webs, hydroentangled spunlace webs, or through air bonded carded webs. Examples of suitable topsheet layer 20 materials can include, but are not limited to, natural fiber webs (such as cotton), rayon, hydroentangled webs, bonded carded webs of polyester, polypropylene, polyethylene, nylon, or other heat-bondable fibers (such as bicomponent fibers), polyolefins, copolymers of polypropylene and polyethylene, linear low-density polyethylene, and aliphatic esters such as polylactic acid. Finely perforated films and net materials can also be used, as can laminates of/or combinations of these materials. An example of a suitable topsheet layer 20 can be a bonded carded web made of polypropylene and polyethylene such as that obtainable from Sandler Corporation, Germany. U.S. Pat. No. 4,801,494 to Datta, et al., and U.S. Pat. No. 4,908,026 to Sukiennik, et al., and WO 2009/062998 to Texol teach various other topsheet materials that may be used as the topsheet layer 20, each of which is hereby incorporated by reference thereto in its entirety. Additional topsheet layer 20 materials can include, but are not limited to, those described in U.S. Pat. No. 4,397,644 to Matthews, et al., U.S. Pat. No. 4,629,643 to Curro, et al., U.S. Pat. No. 5,188,625 to Van Iten, et al., U.S. Pat. No. 5,382,400 to Pike, et al., U.S. Pat. No. 5,533,991 to Kirby, et al., U.S. Pat. No. 6,410,823 to Daley, et al., and U.S. Publication No. 2012/0289917 to Abuto, et al., each of which is hereby incorporated by reference thereto in its entirety.

In various embodiments, the topsheet layer 20 may contain a plurality of apertures (not shown) formed therethrough to permit body exudates to pass more readily into the absorbent core 24. The apertures may be randomly or uniformly arranged throughout the topsheet layer 20. The size, shape, diameter, and number of apertures may be varied to suit an absorbent article's 10 particular needs.

In various embodiments, the topsheet layer 20 can have a basis weight ranging from about 5, 10, 15, 20 or 25 gsm to about 50, 100, 120, 125 or 150 gsm. For example, in an embodiment, a topsheet layer 20 can be constructed from a through air bonded carded web having a basis weight ranging from about 15 gsm to about 100 gsm. In another example, a topsheet layer 20 can be constructed from a through air bonded carded web having a basis weight from about 20 gsm to about 50 gsm, such as a through air bonded carded web that is readily available from nonwoven material manufacturers, such as Xiamen Yanjan Industry, Beijing, DaYuan Nonwoven Fabrics and others.

In various embodiments, the topsheet layer 20 can be at least partially hydrophilic. In various embodiments, a portion of the topsheet layer 20 can be hydrophilic and a portion of the topsheet layer 20 can be hydrophobic. In various embodiments, the portions of the topsheet layer 20 which can be hydrophobic can be either an inherently hydrophobic material or can be a material treated with a hydrophobic coating.

In various embodiments, the topsheet layer 20 can be a multicomponent topsheet layer 20 such as by having two or more different nonwoven or film materials, with the different materials placed in separate locations in the transverse direction (T) of the absorbent article 10. For example, the topsheet layer 20 can be a two layer or multicomponent material having a central portion positioned along and straddling a longitudinal axis 12 of the absorbent article 10 with lateral side portions flanking and bonded to each side edge of the central portion. The central portion can be constructed from a first material and the side portions can be constructed from a material which can be the same as or different from the material of the central portion. In such embodiments, the central portion may be at least partially hydrophilic and the side portions may be inherently hydrophobic or may be treated with a hydrophobic coating. Examples of constructions of multi-component topsheet layers 20 are generally described in U.S. Pat. No. 5,961,505 to Coe, U.S. Pat. No. 5,415,640 to Kirby, and U.S. Pat. No. 6,117,523 to Sugahara, each of which is incorporated herein by reference thereto in its entirety.

Absorbent Core:

An absorbent core 24 can be positioned between the topsheet layer 20 and the backsheet layer 22. The absorbent core 24 can generally be any single layer structure or combination of layer components, which can demonstrate some level of compressibility, conformability, be non-irritating to a wearer's skin, and capable of absorbing and retaining liquids and other body exudates. Additionally, the absorbent core 24 can provide additional capacity to absorb and retain body exudates such as menses. In various embodiments, the absorbent core 24 can be formed from a variety of different materials and can contain any number of desired layers. For example, the absorbent core 24 can include one or more layers (e.g., two layers) of absorbent web material of cellulosic fibers (e.g., wood pulp fibers), other natural fibers, synthetic fibers, woven or nonwoven sheets, scrim netting, or other stabilizing structures, superabsorbent material, binder materials, surfactants, selected hydrophobic and hydrophilic materials, pigments, lotions, odor control agents or the like, as well as combinations thereof. In an embodiment, the absorbent web material can include a matrix of cellulosic fluff and can also include superabsorbent material. The cellulosic fluff can comprise a blend of wood pulp fluff. An example of a wood pulp fluff can be identified with the trade designation NB 416, available from Weyerhaeuser Corp., and is a bleached, highly absorbent wood pulp containing primarily soft wood fibers.

In various embodiments, if desired, the absorbent core 24 can include an optional amount of superabsorbent material. Examples of suitable superabsorbent material can include poly(acrylic acid), poly(methacrylic acid), poly(acrylamide), poly(vinyl ether), maleic anhydride copolymers with vinyl ethers and α-olefins, poly(vinyl pyrrolidone), poly (vinylmorpholinone), poly(vinyl alcohol), and salts and copolymers thereof. Other superabsorbent materials can include unmodified natural polymers and modified natural polymers, such as hydrolyzed acrylonitrile-grafted starch, acrylic acid grafted starch, methyl cellulose, chitosan, carboxymethyl cellulose, hydroxypropyl cellulose, and natural gums, such as alginates, xanthan gum, locust bean gum, and so forth. Mixtures of natural and wholly or partially synthetic superabsorbent polymers can also be useful. The superabsorbent material can be present in the absorbent core 24 in any amount as desired.

Regardless of the combination of absorbent materials used in the absorbent core 24, the absorbent materials can be formed into a web structure by employing various conventional methods and techniques. For example, the absorbent web can be formed by techniques such as, but not limited to, a dry-forming technique, an air forming technique, a wet forming technique, a foam forming technique, or the like, as well as combinations thereof. A coform nonwoven material can also be employed. Methods and apparatus for carrying out such techniques are well known in the art.

The shape of the absorbent core 24 can vary as desired and can comprise any one of various shapes including, but not limited to, triangular, rectangular, dog-bone and elliptical shapes. In various embodiments, the absorbent core 24 can have a shape that generally corresponds with the overall shape of the absorbent article 10. The dimensions of the absorbent core 24 can be substantially similar to those of the absorbent article 10, however, it will be appreciated that the dimensions of the absorbent core 24 while similar, will often be less than those of the overall absorbent article 10, in order to be adequately contained therein.

By way of example, suitable materials and/or structures for the absorbent core 24 can include, but are not limited to, those described in U.S. Pat. No. 4,610,678 to Weisman, et al., U.S. Pat. No. 6,060,636 to Yahiaoui, et al., U.S. Pat. No. 6,610,903 to Latimer, et al., U.S. Pat. No. 7,358,282 to Krueger, et al., and U.S. Publication No. 2010/0174260 to Di Luccio, et al., each of which is hereby incorporated by reference thereto in its entirety.

As described above, in various embodiments, an absorbent core 24 can be a single layer structure and can include, for example, a matrix of cellulosic fluff and superabsorbent material. In various embodiments, an absorbent core 24 can have at least two layers of material, such as, for example, a body facing layer and a garment facing layer. In various embodiments, the two layers can be identical to each other. In various embodiments, the two layers can be different from each other. In such embodiments, the two layers can provide the absorbent article 10 with different absorption properties as deemed suitable. In various embodiments, the body facing layer of the absorbent core 24 may be constructed of an airlaid material and the garment facing layer of the absorbent core 24 may be constructed of a superabsorbent polymer-containing compressed sheet. In such embodiments, the airlaid material can have a basis weight from about 40 to about 200 gsm and the superabsorbent polymer-containing compressed sheet can be a cellulosic fluff based material that can be a combination of cellulosic pulp and SAP enclosed with a tissue carrier and having a basis weight from about 40 to about 400 gsm.

Backsheet Layer:

The backsheet layer 22 is generally liquid impermeable and is the portion of the absorbent article 10 which faces the garment of the wearer. The backsheet layer 22 can permit the passage of air or vapor out of the absorbent article 10 while still blocking the passage of liquids. Any liquid impermeable material may generally be utilized to form the backsheet layer 22. The backsheet layer 22 can be composed of a single layer or multiple layers, and these one or more layers can themselves comprise similar or different materials. Suitable material that may be utilized can be a microporous polymeric film, such as a polyolefin film of polyethylene or polypropylene, nonwovens and nonwoven laminates, and film/nonwoven laminates. The particular structure and composition of the backsheet layer 22 can be selected from various known films and/or fabrics with the particular material being selected as appropriate to provide the desired level of liquid barrier, strength, abrasion resistance, tactile properties, aesthetics and so forth. In various embodiments, a polyethylene film can be utilized that can have a thickness in the range of from about 0.2 or 0.5 mils to about 3.0 or 5.0 mils. An example of a backsheet layer 22 can be a polyethylene film such as that obtainable from Pliant Corporation, Schaumburg, Ill., USA. Another example can include calcium carbonate-filled polypropylene film. In still another embodiment, the backsheet layer 22 can be a hydrophobic nonwoven material with water barrier properties such as a nonwoven laminate, an example of which can be a spunbond, meltblown, meltblown, spunbond, four-layered laminate. The backsheet layer 22 can, therefore, be of a single or multiple layer construction, such as of multiple film layers or laminates of film and nonwoven fibrous layers. Suitable backsheet layers 22 can be constructed from materials such as those described in U.S. Pat. No. 4,578,069 to Whitehead, et al., U.S. Pat. No. 4,376,799 to Tusim, et al., U.S. Pat. No. 5,695,849 to Shawver, et al., U.S. Pat. No. 6,075,179 to McCormack, et al., and U.S. Pat. No. 6,376,095 to Cheung, et al., each of which are hereby incorporated by reference thereto in its entirety.

Additional Layers:

In various embodiments, an absorbent article 10 can optionally include at least one of a fluid intake layer, a transfer delay layer, a surge layer, and/or a distribution layer positioned between the topsheet layer 20 and the backsheet layer 22.

Fluid Intake Layer:

In various embodiments, the absorbent article 10 can include a liquid permeable fluid intake layer (not shown) positioned between the topsheet layer 20 and the absorbent core 24. Such a fluid intake layer 32 can be made of a material that can be capable of rapidly transferring, in the Z-direction, body exudates that are delivered to the topsheet layer 20. The fluid intake layer can generally have any shape and/or size desired. For example, the fluid intake layer can have a length of between about 20, 40 or 60 mm to about 150, 150, 175, 200 or 300 mm and a width of between about 10, 15 or 20 mm to about 60, 80 or 100 mm may be utilized. The fluid intake layer can have a thickness in the depth direction from about 0.5 mm to about 3 mm. Any of a variety of different materials can be capable of being used for the fluid intake layer. The material may be synthetic, cellulosic, or a combination of synthetic and cellulosic materials. The fluid intake layer can be constructed from any woven or nonwoven material. For example, the fluid intake layer can be constructed as an airlaid or TABCW material. For example, airlaid cellulosic tissues may be suitable for use in the fluid intake layer. The airlaid cellulosic tissue may have a basis weight ranging from about 10 or 100 gsm to about 250 or 300 gsm. The airlaid cellulosic tissue can be formed from hardwood and/or softwood fibers. An airlaid cellulosic tissue can have a fine pore structure and can provide an excellent wicking capacity, especially for menses.

Transfer Delay Layer:

In various embodiments, the absorbent article 10 can include a liquid permeable transfer delay layer (not shown) positioned below the topsheet layer 20 in the depth (Z) direction. The transfer delay layer may contain a material that is substantially hydrophobic. For example, the transfer delay layer may be a nonwoven fibrous web composed of relatively hydrophobic materials, such as polypropylene, polyethylene, polyester, or the like, and also may be composed of a blend of such materials. One example of a material suitable for the transfer delay layer can be a spunbond web composed of polypropylene, multi-lobal fibers. Further examples of suitable transfer delay layers can include spunbond webs composed of polypropylene fibers, which may be round, tri-lobal or poly-lobal in cross-sectional shape and which may be hollow or solid in structure. Typically the webs are bonded, such as by thermal bonding, over about 3% to about 30% of the web area. Other examples of suitable materials that may be used for the transfer delay layer are described in U.S. Pat. No. 4,798,603 to Meyer, et al. and U.S. Pat. No. 5,248,309 to Serbiak, et al. The transfer delay layer may generally have any size, such as a length of about 150 mm to about 300 mm. Typically, the length of the transfer delay layer can be approximately equal to the length of the absorbent article 10. The width of the transfer delay layer can be from between about 50 mm to about 75 mm. The transfer delay layer can have a basis weight less than about 250 gsm, and in some embodiments, between about 40 gsm and about 200 gsm.

Surge Layer:

Additional layers between the topsheet layer 20 and the absorbent core 24 can include surge layers as are commonly known. Surge layers (not shown) can be constructed of any woven or nonwoven material that is easily penetrated by body exudates. The surge layers can help to absorb, decelerate, and diffuse surges or gushes of liquid that may be rapidly introduced into the absorbent article 10. The surge layers can rapidly accept and temporarily hold the liquid prior to releasing the liquid into, for instance, the absorbent core 24 or any other layer of the absorbent article 10. Various woven fabrics and nonwoven webs can be used to construct the surge layers. For example, the surge layers can comprise a nonwoven fabric layer composed of a meltblown or spunbond web of polyolefin or polyester filaments. Such nonwoven fabric layers may include conjugate, biconstituent and homopolymer fibers of staple or other lengths and mixtures of such fibers with other types of fibers. The surge layers can also be a bonded card web or an airlaid web composed of natural and/or synthetic fibers. The bonded carded web may, for example, be a powder bonded carded web, an infrared bonded carded web, or a through air bonded carded web. The bonded carded webs can optionally include a mixture or blend of different fibers. The surge layers typically have a basis weight of less than about 100 gsm, and in some embodiments, from about 10 gsm to about 40 gsm.

Distribution Layer:

The absorbent system can have a distribution layer (not shown) positioned below the absorbent core 24. The distribution layer can increase absorbency of the absorbent article 10. The distribution layer can be constructed of various materials such as, but not limited to, hydroentangled webs, through air bonded carded webs, meltblown webs, and meltblown microfiber webs. The distribution layer can include a hydrophilic material. The distribution layer can be smaller in size than the absorbent core 24 of the absorbent article 10. In various embodiments, the distribution layer can have a longitudinal length from about 80, 90, 100, 110, 120, 125 or 130 mm to about 135, 140, 150, 160, 170, 180 or 190 mm and can have a transverse width from about 30, 35 or 40 mm to about 45, 50, 55 or 60 mm. In various embodiments, the distribution layer 40 can have a basis weight from about 10, 20, 25, 30 or 50 gsm to about 60, 70, 80, 90, 100, 120, 140, 150, 160, 180 or 200 gsm.

Wings:

The wings, 60 and 62, can be constructed from materials described above with respect to the topsheet layer 20 and the backsheet layer 22. In various embodiments, the wings, 60 and 62, can comprise an extension of a layer of material within the topsheet layer 20 and/or the backsheet layer 22. For example, the wings, 60 and 62, can be formed by an extension of the topsheet layer 20 and backsheet layer 22 that are then bonded together to form portions of the sealed peripheral region 38. Such wings, 60 and 62, can be integrally formed with the main portion of the absorbent article 10. Alternatively, the wings, 60 and 62, can be formed independently and separately attached to the central portion 54 of the absorbent article 10. Wings, 60 and 62, that are made independent of the other components of the absorbent article 10 can be bonded to a portion of the topsheet layer 20 and/or backsheet layer 22. Examples of processes for manufacturing absorbent articles 10 and wings, 60 and 62, include, but are not limited to, those described in U.S. Pat. No. 4,059,114 to Richards, U.S. Pat. No. 4,862,574 to Hassim, et al., U.S. Pat. No. 5,342,647 to Heindel, et al., U.S. Pat. No. 7,070,672 to Alcantara, et al., U.S. Publication No. 2004/0040650 to Venturino, et al., and international publication WO1997/040804 to Emenaker, et al., each of which are hereby incorporated by reference thereto in its entirety.

Mechanical Garment Attachment:

The absorbent article 10 can be provided with a primary mechanical garment attachment 70 to keep the absorbent article 10 securely and properly positioned in the wearer's undergarment. The primary mechanical garment attachment 70 can be, for example, a suitable hook component such as a J-hook, mushroom-head hook, flat-top nail-head hook, a palm-tree hook, a multiple-J hook, or the like, as well as combinations thereof. In various embodiments, the primary mechanical garment attachment 70 may be bonded directly to the garment facing surface 26 of the absorbent article 10, such as, for example, the garment facing surface 26 of the backsheet layer 22. In various embodiments, the backsheet layer 22 of the absorbent article 10 can be a stretchable material. In various embodiments, the backsheet layer 22 of the absorbent article 10 can be an elastic material. In various embodiments, the backsheet layer 22 of the absorbent article 10 can be a mesh material. In various embodiments, the primary mechanical garment attachment 70 may be bonded indirectly to the garment facing surface 26 of the absorbent article 10, such as, for example being bonded to a base substrate wherein the base substrate is subsequently bonded directly to the garment facing surface 26 of the absorbent article 10. In various embodiments, the base substrate can be a stretchable material. In various embodiments, the base substrate can be an elastic material. In various embodiments, the base substrate can be a mesh material.

The primary mechanical garment attachment 70 can be positioned in a primary garment attachment region 72 and can be located on a garment facing surface 26 of the absorbent article 10. In various embodiments, the absorbent article 10 can have at least one pair of opposing primary garment attachment regions 72. In various embodiments, such as, for example, illustrated in FIGS. 3 and 4, the absorbent article 10 can have at least two pairs of opposing primary garment attachment regions, first pair 72A and 72B and second pair 72C and 72D. In various embodiments, the absorbent article 10 can have at least three pairs of opposing primary garment attachment regions 72.

Each primary garment attachment region 72 can have a leading portion 64, defined by the primary mechanical garment attachment 70 closest to the longitudinal axis 12, and a trailing portion 66, defined by the primary mechanical garment attachment 70 furthest from the longitudinal axis 12. In various embodiments, a primary garment attachment region 72 can have a leading portion 64 which can be substantially adjacent to, without crossing, the longitudinal axis 12 of the absorbent article 10. In various embodiments, a leading portion 64 of a primary garment attachment region 72 can be no closer than a distance of 1, 2, 3, 4, or 5 mm to the longitudinal axis 12. In various embodiments, a primary garment attachment region 72 can have a trailing portion 66 which can be substantially adjacent to, without entering into, the sealed peripheral region 38. In various embodiments, a trailing portion 66 of a primary garment attachment region 72 can be no closer than a distance of 1, 2, 3, 4, or 5 mm to the sealed peripheral region 38. In various embodiments, a primary garment attachment region 72 can have a leading portion 64 which can be any distance from the longitudinal axis 12 as deemed suitable and a trailing portion 66 which can be any distance from the sealed peripheral region 38 as deemed suitable. Each primary garment attachment region 72 can have a length 74 which can be measured as the distance from the leading portion 64 to the training portion 66. In various embodiments, the length 74 of each primary garment attachment region 72 can be at least about 20 mm. In various embodiments, the length 74 of each primary garment attachment region 72 can be at least about 20, 25, 30, 35, 40, 45, 50, 55, 60, 65, 70, or 75 mm. In various embodiments, the length 74 of each primary garment attachment region 72 can be from about 20, 25, 30, 35, 40, 45, or 50 mm to about 55, 60, 65, 70, 75, 80, 85 or 90 mm. Each primary garment attachment region 72 can also have a pair of opposing side portions, 68A and 68B, which extend from the leading portion 64 to the trailing portion 66 of the primary garment attachment region 72. Each side portion, 68A and 68B, is defined by the presence of a primary mechanical garment attachment 70. In various embodiments, each of the side portions, 68A and 68B, can be straight as they extend between the leading portion 64 and the trailing portion 66 and/or can contain an arcuate region as they extend between the leading portion 64 and the trailing portion 66. Each primary garment attachment region 72 can have a width 76 which can be measured as the distance between the opposing side portions, 68A and 68B. In various embodiments, the width 76 of each primary garment attachment region 72 can be at least about 2 mm. In various embodiments, the width 76 of each primary garment attachment region 72 can be at least about 2, 3, 4, 5, 6, 7, 8, 9, or 10 mm. In various embodiments, the width 76 of each primary garment attachment region 72 can be from about 2, 3, 4, 5, 6 or 7 mm to about 8, 9, 10, 11, 12, 13, 14 or 15 mm. The length 74 and width 76 of each primary garment attachment region 72 can provide an area for each primary attachment region 72 which can contain the primary mechanical garment attachment 70. In various embodiments, the area of a primary garment attachment region 72 can present an overall shape or appearance to the primary garment attachment region 72. In various embodiments, an overall shape or appearance of a primary garment attachment region 72 can be square, rectangular, circular, oval, arcuate, or wavelike.

The length 74 of each of the primary garment attachment regions 72 can be divided into three segments: a first segment 80, a second segment 82 and a third segment 84. In various embodiments, each of the three segments, 80, 82 and 84, can be equal in length. In various embodiments, two of the three segments, 80, 82 or 84, can be equal in length and one of the three segments, 80, 82 or 84, can have a length different from the other two segments, 80, 82 or 84. In various embodiments, each of the three segments, 80, 82 and 84, can have a length different from each of the other segments, 80, 82 and 84. The first segment 80 of the primary garment attachment region 72 can be the portion of the primary garment attachment region 72 positioned in a chassis area 90 of the absorbent article 10 and which underlays the absorbent core 24 when viewing the absorbent article 10 in a top down configuration. The primary mechanical garment attachment 70 positioned in the first segment 80 of the primary garment attachment region 72 can maintain contact between the absorbent article 10 and the wearer facing surface of the wearer's undergarment 16 when the absorbent article 10 is in a second configuration such as a usage configuration. The second segment 82 of the primary garment attachment region 72 can be the portion of the primary garment attachment region 72 positioned in the wing folding area 92. The primary mechanical garment attachment 70 positioned in the second segment 82 of the primary garment attachment region 72 can maintain contact between the absorbent article 10 and each of the surfaces of the seams of the wearer's undergarment 16—the wearer facing surface of the seam, the thigh facing surface of the seam and the garment facing surface of the seam when the absorbent article 10 is in a second configuration such as a usage configuration. The third segment 84 of the primary garment attachment region 72 can be the portion of the primary garment attachment region 72 positioned in a wing area 94. The primary mechanical garment attachment 70 positioned in the third segment 84 of the primary garment attachment region 72 can maintain contact between the absorbent article 10 and the garment facing surface 18 of the wearer's undergarment 16 when the absorbent article 10 is in a second configuration such as a usage configuration.

Referring to FIG. 3, the primary mechanical garment attachment 70 positioned within the primary garment attachment region 72 is illustrated in an exemplary configuration of consecutive rows of mechanical garment attachments such as hooks. In various embodiments, such as, for example, an embodiment in which the mechanical garment attachment is bonded indirectly to the backsheet layer 22 of the absorbent article 10, it may be desirable to incorporate score lines into the base substrate. It is believed that such score lines can assist with enabling the folding of the wings, 60 and 62, about the wearer's undergarment. In various embodiments, at least one score line can be incorporated into the base substrate positioned in the second segment of the primary garment attachment region 72.

In various embodiments, the mechanical garment attachments 70 can be positioned in the primary garment attachment region 72 in a pattern such as, for example, a spaced apart configuration. For example, within a primary garment attachment region 72 a row of hooks can be followed by an area of the primary garment attachment region 72 without hooks which can be followed by another row of hooks and this alternating pattern of rows of hooks and areas without hooks can extend for a least a portion of the primary garment attachment region 72 and, in some embodiments, for the entire length of the primary garment attachment region 72. In various embodiments, a segment, 80, 82, or 84, of a primary garment attachment region 72 can have mechanical garment attachments 70 positioned therein in a consecutive manner such as, for example, consecutive rows of hooks, and a segment, 80, 82, or 84, of a primary garment attachment region 72 can have mechanical garment attachments 70 positioned therein, in a pattern, such as, for example, a spaced apart configuration. In various embodiments, the second segment 82 of a primary garment attachment region 72 can have mechanical garment attachments 70, such as hooks, positioned therein in a spaced apart configuration, and at least one of the first segment 80 and/or the third segment 84 can have mechanical garment attachments 70, such as hooks, positioned therein in a pattern of consecutive rows.

Each of the primary garment attachment regions 72 can be configured to provide the absorbent article 10, when the absorbent article 10 is in a first configuration such as an unfolded and flat configuration, with a primary garment attachment region angle 100. The primary garment attachment region angle 100 is the angle between the longitudinal axis 12 and a line 106 that can be drawn and which connects the middle-width 104 at the trailing portion 66 of the primary garment attachment region 72 with the middle-width 102 at the leading portion 64 of the primary garment attachment region 72 and then extends to the longitudinal axis 12. The primary garment attachment region angle 100, relative to the longitudinal axis 12, can be from about 15, 20, 25, 30 or 35 degrees to about 40, 45, 50, 55, 60, 65 or 70 degrees.

To convert the absorbent article 10 from the first configuration to the second configuration, each wing, 60 and 62, can be folded downwardly in the wing folding areas 92 and can fold under the crotch region of the wearer's undergarment 16. The primary mechanical garment attachment 70 can form a secure attachment to the surface of the wearer's undergarment 16 via each of the three segments, 80, 82 and 84, of the primary garment attachment region 72. FIG. 4 illustrates an absorbent article 10 in a second configuration, a usage configuration, in which the wings, 60 and 62, have been folded downwardly and the primary garment attachment regions, 72A, 72B, 72C and 72D, provide attachment points between the absorbent article 10 and the wearer's undergarment 16. For clarity within the illustration of FIG. 4, the area of each of the primary garment attachment regions 72 are outlined in a broken line and the primary mechanical garment attachment 70 have not been shown in this illustration.

Figure 5:
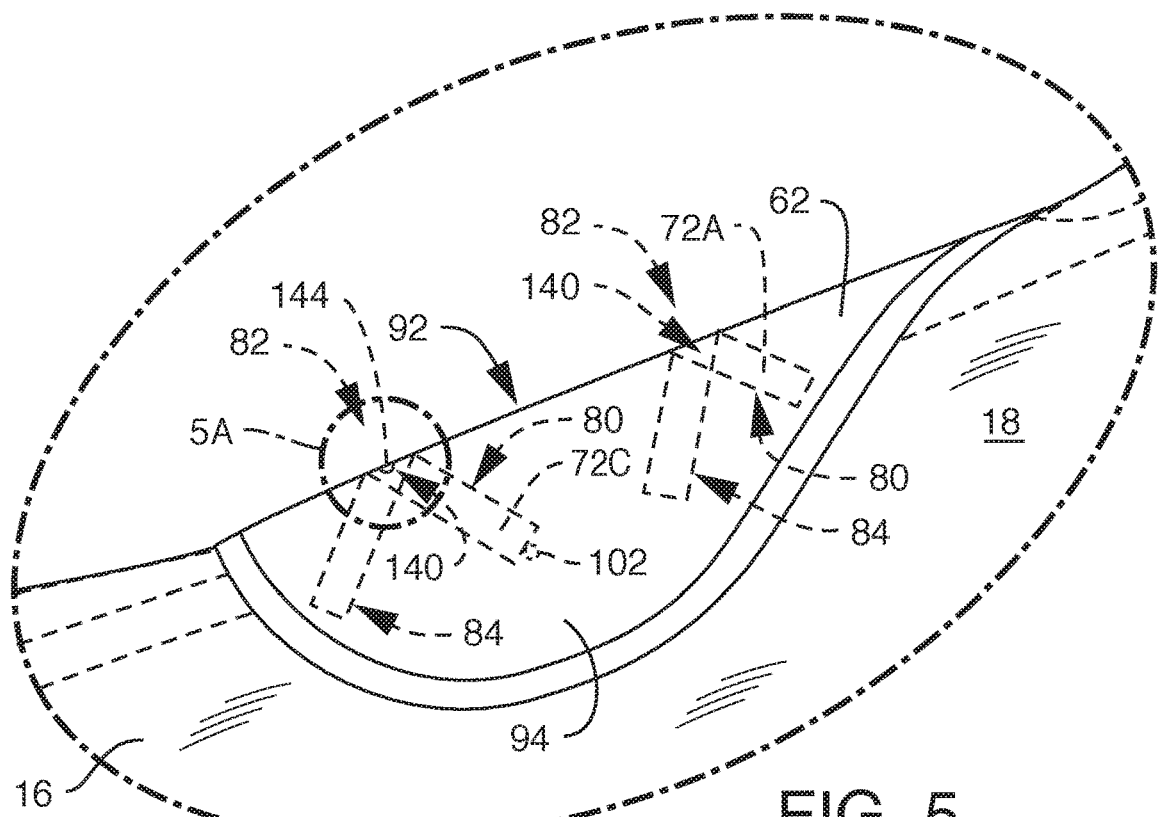
FIG. 5 is a close-up view of a wing and garment attachment region of the absorbent article of FIG. 4.
Figure 5A:
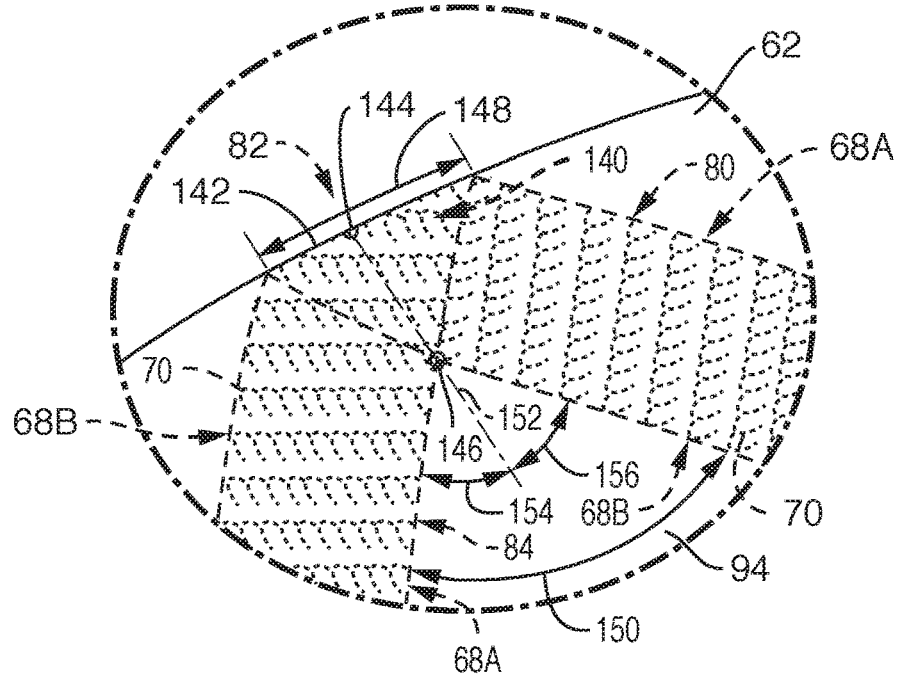
FIG. 5A is a close-up view of a garment attachment region of the absorbent article of FIG. 5.

Referring to FIGS. 5 and 5A, close-up views of the wrapping of a primary garment attachment region 72 when the absorbent article 10 is in a second configuration, a usage configuration, are illustrated. FIG. 5 provides a close-up view of wing 62 and the primary garment attachment regions, 72A and 72C, in a second configuration, a usage configuration. For clarity within the illustration of FIG. 5, the area of each of the primary garment attachment regions, 72A and 72C, is outlined in broken lines and the primary mechanical garment attachment 70 have not been shown in this illustration. FIG. 5A provides a close-up view of the overlap region 140 of a primary garment attachment region 72, such as primary garment attachment region 72C. As can be seen in FIG. 5, when the wing 62 has been converted from a first configuration to a second configuration to place the absorbent article 10 in use in a wearer's undergarment 16, the primary garment attachment regions, 72A and 72C, wrap about the edge of a wearer's undergarment 16 such that the first segment 80 of each primary garment attachment region, 72A and 72C, can attach to the wearer facing surface of the wearer's undergarment 16, the second segments 82 of each primary garment attachment region, 72A and 72C, can wrap around and attach to each of the wearer facing surface, the thigh facing surface and the garment facing surface 18 of the wearer's undergarment 16, particularly in the region of the seam of the wearer's undergarment 16, and the third segment 84 can attach to the garment facing surface 18 of the wearer's undergarment 16. As can be seen in FIGS. 5 and 5A, when the primary garment attachment region 72 is wrapped about the wearer's undergarment, an overlap region 140 is created wherein the second segment 82 of the primary garment attachment region 72 overlaps itself. It is to be understood that the material of the wearer's undergarment is positioned between the two layers of the primary garment attachment region 72 and, therefore, between the overlapping of the second segment 82 upon itself. It is also to be understood that the wearer may not wrap the wing, such as wing 62, tightly to the wearer's undergarment and a portion of the second segment 82 may extend beyond the edge of the material of the wearer's undergarment and, therefore, a portion of the second segment 82 may directly contact and overlap another portion of the second segment 82 in a region which extends beyond the edge of the wearer's undergarment. Due to the shape, configuration, and the primary garment attachment region angle 100 of the primary garment attachment region 72, the overlap region 140 can have a shape such as a triangle. One side of the triangle of the overlap region 140 can be a fold 142 which can be formed in the primary garment attachment region 72 when the wing, such as wing 62, is folded downwardly to convert the absorbent article 10 from the first configuration to the second configuration. The fold 142 can have a length 148 which can be from about 2, 3, 4, 5, 10, 15, 20 or 25 mm to about 30, 35, 40, 45 or 50 mm. The fold 142 can have a mid-point 144 which can be the middle of the fold length 148.

As can be seen in FIGS. 5 and 5A, when the primary garment attachment region 72 is wrapped about the material of the wearer's undergarment 16, the third segment 84 of the primary garment attachment region 72 has been re-positioned and an angle 150 has been created between the first segment 80 and the third segment 84. It is believed that the presence of angle 150 will provide the primary garment attachment region 72 with flexibility such that the primary garment attachment region 72 can absorb the wearer's active movement and will allow the primary garment attachment 70 to remain attached to the wearer's undergarment 16. It is believed that such flexibility in the primary garment attachment region 72 will allow the first segment 80 and the third segment 84 to flex and move with the wearer's active movement. In various embodiments, a line 152 can be drawn from the mid-point 144 of the fold 142 and can extend through the apex 146 of the triangle created by the overlap region 140 and can continue in a direction perpendicular 12 to the longitudinal axis of the absorbent article 10. A first angle 154 can be measured as the angle between side portion 68A of the third segment 84 and the line 152. The first angle 154 can be from about 15, 20, 25, 30 or 35 degrees to about 40, 45, 50, 55, 60, 65 or 70 degrees. A second angle 156 can be measured as the angle between the side portion 68B of the first segment 80 and the line 152. The second angle 156 can be from about 15, 20, 25, 30 or 35 degrees to about 40, 45, 50, 55, 60, 65 or 70 degrees. The angle 150 between the first segment 80 and the third segment 84 when the absorbent article 10 is in a second configuration can be the sum of the first angle 154 and the second angle 156. In various embodiments, the angle 150 between the first segment 90 and the third segment 84 when the absorbent article 10 is in a second configuration can be from about 30, 35, 40, 45, 50, 55, 60, 65, 70, 75, 80 or 85 degrees to about 90, 95, 100, 105, 110, 115, 120, 125, 130, 135 or 140 degrees.

Figure 6:
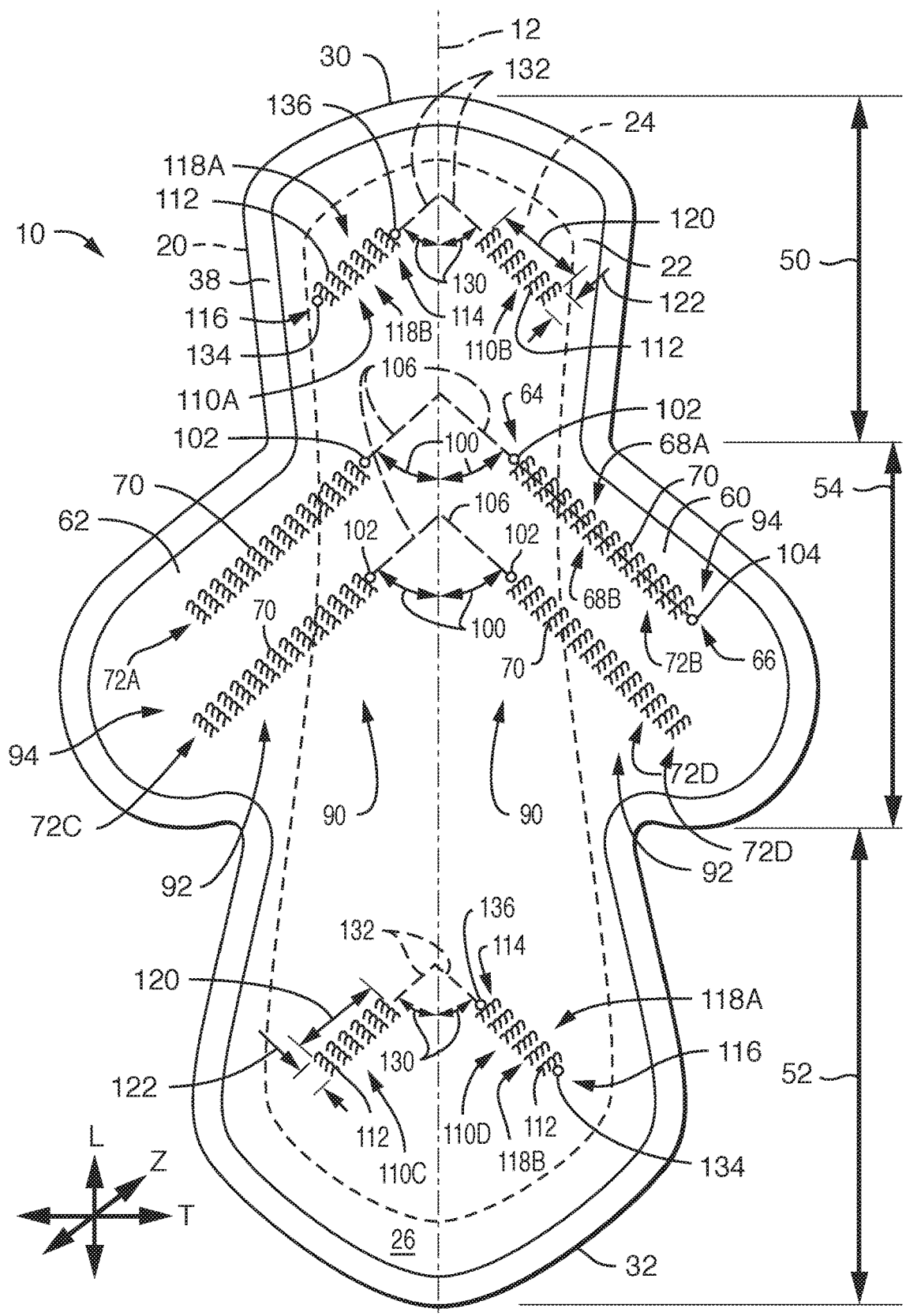
FIG. 6 is bottom view of an embodiment of an absorbent article in a first configuration, such as an unfolded and laid-flat configuration.

Referring to FIG. 6, an embodiment of an absorbent article 10 is illustrated. The absorbent article 10 has two pairs of primary garment attachment regions, first pair 72A and 72B and second pair 72C and 72D. The primary garment attachment regions, 72A, 72B, 72C and 72D, can be as described with reference to FIG. 3. In addition to the two pairs of opposing primary garment attachment regions, 72A, 72B, 72C and 72D, the absorbent article 10 can have at least one opposing pair of secondary garment attachment regions 110 which can each have a secondary garment attachment 112. In such embodiments, the at least one pair of secondary garment attachment regions 110 can be positioned in the anterior portion 50 the posterior portion 52 of the absorbent article 10. In various embodiments, such as illustrated in FIG. 6, the absorbent article 10 can have at least two pairs of opposing secondary garment attachment regions, 110A, 110B, 110C and 110D. In such embodiments, each of the pairs of opposing secondary garment attachment regions 110 can be positioned in the anterior portion 50, the posterior portion 52, or one pair of the opposing secondary garment attachment regions 110 can be positioned in the anterior portion 50 and one pair of the opposing secondary garment attachment regions 110 can be positioned in the posterior portion 52 of the absorbent article 10. In the embodiment of the absorbent article 10 illustrated in FIG. 6, a pair of opposing secondary garment attachment regions, 110A and 110B, are positioned in the anterior portion 50 of the absorbent article 10 and the second pair of opposing garment attachment regions, 110C and 110D, are positioned in the posterior region 52 of the absorbent article 10. In various embodiments, an opposing pair of secondary garment attachment regions 110 can be positioned in the wing areas 94 of the absorbent article 10.

Each secondary garment attachment region 110 can have a leading portion 114, defined by the secondary mechanical garment attachment 112 closest to the longitudinal axis 12, and a trailing portion 116, defined by the secondary garment attachment 112 furthest from the longitudinal axis 12. In various embodiments, a secondary garment attachment region 110 can have a leading portion 114 which can be substantially adjacent to, without crossing, the longitudinal axis 12 of the absorbent article 10. In various embodiments, a leading portion 110 of a secondary garment attachment region 110 can be no closer than a distance of 1, 2, 3, 4 or 5 mm to the longitudinal axis 12. In various embodiments, a secondary garment attachment region 110 can have a trailing portion 116 which can be substantially adjacent to, without entering into, the sealed peripheral region 38. In various embodiments, a trailing portion 116 of a secondary garment attachment region 110 can be no closer than a distance of 1, 2, 3, 4 or 5 mm to the sealed peripheral region 38. Each secondary garment attachment region 110 can have a length 120 which can be measured as the distance from the leading portion 114 to the trailing portion 116. In various embodiments, the length 120 of each secondary garment attachment region 110 can be at least about 15 mm. In various embodiments, the length 120 of each secondary garment attachment region 110 can be at least about 15, 20, 25, 30, 35, 40, 45 or 50 mm. In various embodiments, the length 120 of each secondary garment attachment region 110 can be from about 15, 20 or 25 mm to about 30, 35, 40, 45, or 50 mm. Each secondary garment attachment region 110 can also have a pair of opposing side portions, 118A and 118B, which extend from the leading portion 114 to the trailing portion 116 of the secondary garment attachment region 110. Each side portion, 118A and 118B, is defined by the presence of a secondary mechanical attachment 112. In various embodiments, each of the side portions, 118A and 118B, can be straight as they extend between the leading portion 114 and the trailing portion 116 and/or can contain an arcuate region as they extend between the leading portion 114 and the trailing portion 116. Each secondary garment attachment region 110 can have a width 122 which can be measured as the distance between the opposing side portions, 118A and 118B. In various embodiments, the width 122 of each secondary garment attachment region 110 can be at least about 2 mm. In various embodiments, the width 122 of each secondary garment attachment region 110 can be at least about 2, 3, 4, 5, 6, 7, 8, 9, or 10 mm. In various embodiments, the width 122 of each secondary garment attachment region 110 can be from about 2, 3, 4, 5, 6 or 7 mm to about 8, 9, 10, 11, 12, 13, 14 or 15 mm. The length 120 and width 122 of each secondary garment attachment region 110 can provide an area for each secondary attachment region 110 which can contain the secondary mechanical garment attachment 112. In various embodiments, the area of a secondary garment attachment region 110 can present an overall shape or appearance to the secondary garment attachment region 110. In various embodiments, an overall shape or appearance of a secondary garment attachment region 110 can be square, rectangular, circular, oval, arcuate, or wavelike. In various embodiments, each pair of secondary garment attachment regions 110 positioned on the absorbent article 10 can have the same length 120 and the same width 122 as any other pair of secondary garment attachment regions 110 positioned on the absorbent article 10. In various embodiments, each pair of secondary garment attachment regions 110 positioned on the absorbent article 10 can have a length 120 and a width 122 which are different from the length 120 and width 122 of another pair of secondary garment attachment regions 110 positioned on the absorbent article 10.

Each of the secondary garment attachment regions 110 can be configured to provide the absorbent article 10, when the absorbent article 10 is in a first configuration such as an unfolded and flat configuration, with a secondary garment attachment region angle 130. The secondary garment attachment region angle 130 is the angle between the longitudinal axis 12 and a line 132 that can be drawn and which connects the middle-width 134 at the trailing portion 116 of the secondary garment attachment region 110 with the middle-width 136 at the leading portion 114 of the secondary garment attachment region 110 and then extends to the longitudinal axis 12. The secondary garment attachment region angle 100, relative to the longitudinal axis 12, can be from about 15, 20, 25, 30 or 35 degrees to about 40, 45, 50, 55, 60, 65 or 70 degrees.

Figure 7:
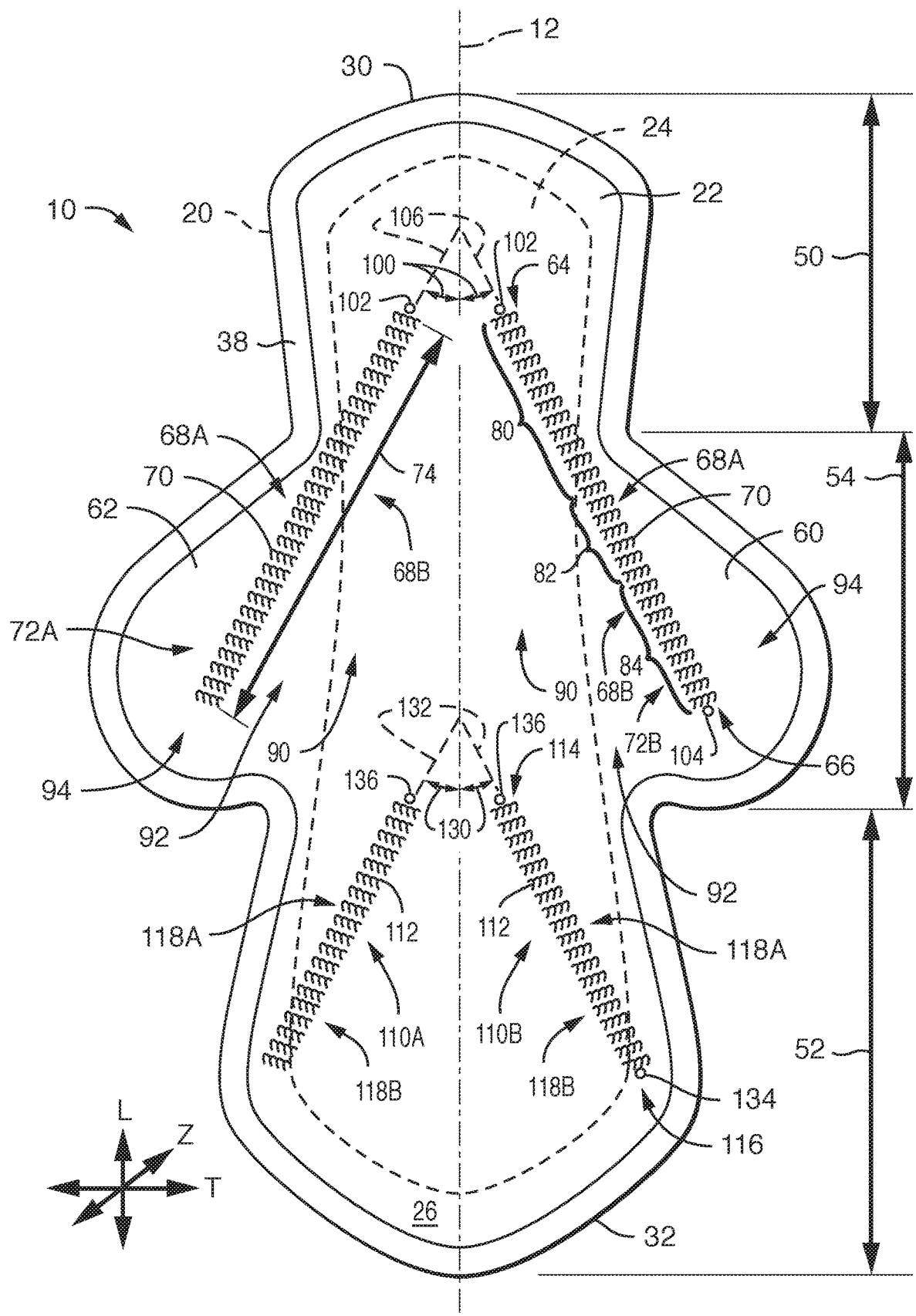
FIG. 7 is a bottom view of an embodiment of an absorbent article in a first configuration, such as an unfolded and laid-flat configuration.

Referring to FIG. 7, an embodiment of an absorbent article 10 is illustrated. The absorbent article 10 has a single pair of primary garment attachment regions, 72A and 72B. The primary garment attachment regions, 72A and 72B, can each have a leading portion 64, defined by the primary mechanical garment attachment 70 closest to the longitudinal axis 12, and a trailing portion 66, defined by the primary mechanical garment attachment 70 furthest from the longitudinal axis 12. Each primary garment attachment region, 72A and 72B, can have a length 74 which can be measured as the distance from the leading portion 64 to the training portion 66. As illustrated in FIG. 7, in various embodiments, the primary garment attachment regions, 72A and 72B, can extend from the central portion 54 of the absorbent article 10 into the anterior portion 50 of the absorbent article 10. In various embodiments, the absorbent article 10 can have a single pair of wings, 60 and 62, such as illustrated in FIG. 7. In various embodiments, the absorbent article 10 can have more than one pair of wings, 60 and 62, and each pair of wings, 60 and 62, can be affiliated with a primary garment attachment region 72.

As illustrated in FIG. 7, the length 74 of each of the primary garment attachment regions 72 can be divided into three segments: a first segment 80, a second segment 82 and a third segment 84. The first segment 80 of the primary garment attachment region 72 can be the portion of the primary garment attachment region 72 positioned in a chassis area 90 of the absorbent article 10 and which underlays the absorbent core 24 when viewing the absorbent article 10 in a top down configuration. The second segment 82 of the primary garment attachment region 72 can be the portion of the primary garment attachment region 72 positioned in the wing folding area 92. The third segment 84 of the primary garment attachment region 72 can be the portion of the primary garment attachment region 72 positioned in a wing area 94.

Each of the primary garment attachment regions 72 can be configured to provide the absorbent article 10, when the absorbent article 10 is in a first configuration such as an unfolded and flat configuration, with a primary garment attachment region angle 100. The primary garment attachment region angle 100 is the angle between the longitudinal axis 12 and a line 106 that connects the middle-width 104 at the trailing portion 66 of the primary garment attachment region 72 with the middle-width 102 at the leading portion 64 of the primary garment attachment region 72 and then extends to the longitudinal axis 12. The primary garment attachment region angle 100, relative to the longitudinal axis 12, can be from about 15, 20, 25, 30 or 35 degrees to about 40, 45, 50, 55, 60, 65 or 70 degrees.

In addition to the pair of opposing primary garment attachment regions, 72A and 72B, the absorbent article 10 can have at least one opposing pair of secondary garment attachment regions 110 which can each have a secondary garment attachment 112. As illustrated in FIG. 7, the at least one pair of secondary garment attachment regions 110 can be positioned in the posterior portion 52 of the absorbent article 10. Each secondary garment attachment region 110 can have a leading portion 114, defined by the secondary mechanical garment attachment 112 closest to the longitudinal axis 12, and a trailing portion 116, defined by the secondary garment attachment 112 furthest from the longitudinal axis 12. Each secondary garment attachment region 110 can have a length 120 which can be measured as the distance from the leading portion 114 to the trailing portion 116. The length 120 and width 122 of each secondary garment attachment region 110 can provide an area for each secondary attachment region 110 which can contain the secondary mechanical garment attachment 112. In various embodiments, each pair of secondary garment attachment regions 110 positioned on the absorbent article 10 can have the same length 120 and the same width 122 as any other pair of secondary garment attachment regions 110 positioned on the absorbent article 10. In various embodiments, each pair of secondary garment attachment regions 110 positioned on the absorbent article 10 can have a length 120 and a width 122 which are different from the length 120 and width 122 of another pair of secondary garment attachment regions 110 positioned on the absorbent article 10.

Each of the secondary garment attachment regions 110 can be configured to provide the absorbent article 10, when the absorbent article 10 is in a first configuration such as an unfolded and flat configuration, with a secondary garment attachment region angle 130. The secondary garment attachment region angle 130 is the angle between the longitudinal axis 12 and a line 132 that connects the middle-width 134 at the trailing portion 116 of the secondary garment attachment region 110 with the middle-width 136 at the leading portion 114 of the secondary garment attachment region 110 and then extends to the longitudinal axis 12. The secondary garment attachment region angle 100, relative to the longitudinal axis 12, can be from about 15, 20, 25, 30 or 35 degrees to about 40, 45, 50, 55, 60, 65 or 70 degrees.

In the interests of brevity and conciseness, any ranges of values set forth in this disclosure contemplate all values within the range and are to be construed as support for claims reciting any sub-ranges having endpoints which are whole number values within the specified range in question. By way of hypothetical example, a disclosure of a range of from 1 to 5 shall be considered to support claims to any of the following ranges: 1 to 5; 1 to 4; 1 to 3; 1 to 2; 2 to 5; 2 to 4; 2 to 3; 3 to 5; 3 to 4; and 4 to 5.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
   a. a longitudinal axis and a transverse axis;
   b. an anterior portion, a posterior portion, and a central portion extending between the anterior portion and the posterior portion;
   c. a topsheet layer, a backsheet layer, and an absorbent core positioned between the topsheet layer and the backsheet layer;
   d. a first wing extending in a first transverse direction and a second wing extending in a second transverse direction which is opposite the first transverse direction;
   e. a pair of opposing primary garment attachment regions, each of the primary garment attachment regions having a first segment positioned in a chassis area of the absorbent article, a second segment positioned in a wing folding area of the absorbent article, and a third segment positioned in a wing area of the absorbent article; and
   f. a mechanical garment attachment positioned within each of the primary garment attachment regions.

2. The absorbent article of claim 1 wherein each primary garment attachment region has a primary garment attachment region angle relative to the longitudinal axis from about 15 degrees to about 70 degrees.

3. The absorbent article of claim 1 wherein each primary garment attachment region has a width from about 2 mm to about 15 mm.

4. The absorbent article of claim 1 wherein each primary garment attachment region has a length from about 20 mm to about 90 mm.

5. The absorbent article of claim 1 further comprising a second pair of opposing primary garment attachment regions.

6. The absorbent article of claim 1 further comprising a pair of opposing secondary garment attachment regions.

7. The absorbent article of claim 6 wherein the pair of opposing secondary garment attachment regions are positioned in the anterior portion of the absorbent article.

8. The absorbent article of claim 6 wherein the pair of opposing secondary garment attachment regions are positioned in the posterior portion of the absorbent article.

9. The absorbent article of claim 6 wherein each of the secondary garment attachment regions has a secondary garment attachment region angle relative to the longitudinal axis from about 15 degrees to about 70 degrees.

10. The absorbent article of claim 6 wherein each of the secondary garment attachment regions has a width from about 2 mm to about 15 mm.

11. The absorbent article of claim 6 wherein each of the secondary garment attachment regions has a length from about 15 mm to about 50 mm.

12. The absorbent article of claim 1 wherein the second segment of each of the primary garment attachment regions comprises a plurality of mechanical garment attachments positioned therein wherein the mechanical garment attachments are positioned in a plurality of rows of the mechanical garment attachments and a first row of plurality of rows of the mechanical garment attachments is in a spaced apart configuration from a second row of the plurality of rows of the mechanical garment attachments.

13. The absorbent article of claim 1 wherein the mechanical garment attachment is bonded directly to a base substrate wherein the base substrate is bonded directly to the backsheet layer of the absorbent article.

14. The absorbent article of claim 13 wherein a score line is incorporated into the base substrate.

* * * * *